US009428521B2

(12) United States Patent
Suzuki et al.

(10) Patent No.: US 9,428,521 B2
(45) Date of Patent: Aug. 30, 2016

(54) PROCESS FOR THE PRODUCTION OF A CARBODIIMIDE

(75) Inventors: Kenji Suzuki, Kawaguchi (JP); Tsukasa Kato, Kawaguchi (JP); Tsutomu Yamada, Kawaguchi (JP); Yuya Kamada, Kawaguchi (JP); Shinichiro Shoji, Iwakuni (JP)

(73) Assignees: KAWAGUCHI CHEMICAL INDUSTRY CO., LTD., Tokyo (JP); TEIJIN LIMITED, Osaka (JP)

( * ) Notice: Subject to any disclaimer, the term of this patent is extended or adjusted under 35 U.S.C. 154(b) by 0 days.

(21) Appl. No.: 13/704,117

(22) PCT Filed: Jun. 15, 2011

(86) PCT No.: PCT/JP2011/064193
§ 371 (c)(1),
(2), (4) Date: Dec. 13, 2012

(87) PCT Pub. No.: WO2011/158958
PCT Pub. Date: Dec. 22, 2011

(65) Prior Publication Data
US 2013/0085274 A1   Apr. 4, 2013

(30) Foreign Application Priority Data

Jun. 16, 2010  (JP) ................... 2010-137173
Jun. 16, 2010  (JP) ................... 2010-137174

(51) Int. Cl.
*C07D 498/10*   (2006.01)
*B01J 31/02*   (2006.01)

(52) U.S. Cl.
CPC .......... *C07D 498/10* (2013.01); *B01J 31/0239* (2013.01); *B01J 2231/40* (2013.01)

(58) Field of Classification Search
CPC .................................................. C07D 498/10
USPC ....................................................... 540/453
See application file for complete search history.

(56) References Cited

U.S. PATENT DOCUMENTS

2011/0251384 A1  10/2011  Shoji et al.

FOREIGN PATENT DOCUMENTS

| JP | 2004-332166 A | 11/2004 |
| JP | 2005-350829 A | 12/2005 |
| WO | 2008/081230 A1 | 7/2008 |
| WO | 2010/071211 A1 | 6/2010 |

OTHER PUBLICATIONS

Pedro Molina, et al., "A New and Efficient Preparation of Cyclic Carbodiimides from Bis(iminophosphoranes) and the System Boc₂O/DMAP", Journal of Organic Chemistry, 1994, pp. 7306-7315, vol. 59.
International Preliminary Report on Patentability for International Application No. PCT/JP2011/064193 dated Jan. 24, 2013.

*Primary Examiner* — Bruck Kifle
(74) *Attorney, Agent, or Firm* — Sughrue Mion, PLLC

(57) ABSTRACT

A process for the production of a carbodiimide, comprising the steps of:
(1) reacting an amine represented by the following formula (A) with carbon disulfide in the presence of a catalyst at a reaction temperature of 50 to 150° C. to obtain a thiourea represented by the following formula (B):

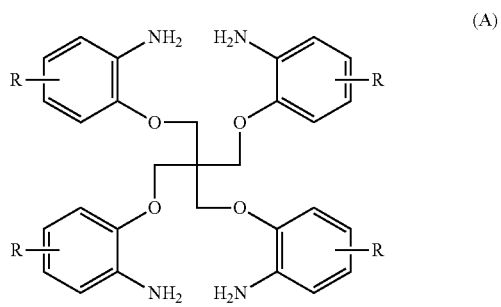

(In the above formula (A), R is a hydrogen atom or an alkyl group having 1 to 6 carbon atoms.)

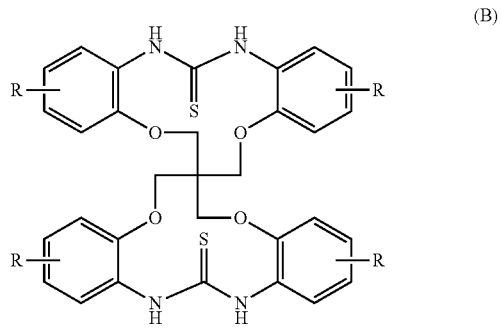

(In the above formula (B), R is as defined in the above formula (A);
(2) desulfurizing the obtained thiourea with a hypochlorite in the presence of a basic compound to obtain a carbodiimide represented by the following formula (C):

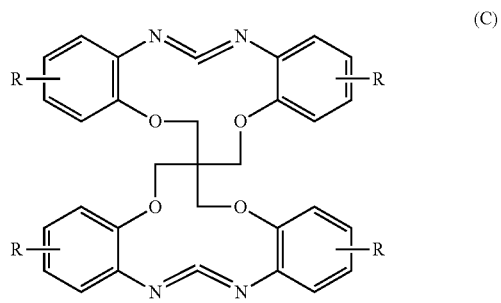

(In the above formula (C), R is as defined in the above formula (A)); and
(3) purifying the obtained carbodiimide.

12 Claims, No Drawings

PROCESS FOR THE PRODUCTION OF A CARBODIIMIDE

TECHNICAL FIELD

The present invention relates to a process for the production of a carbodiimide and, more specifically, to a process for the production of a specific carbodiimide.

BACKGROUND ART

It is proposed that the concentration of carboxyl groups should be reduced by using a sealant for carboxyl groups since the hydrolysis of a compound having an ester bond such as a polyester is promoted by a polar group such as a carboxyl group (Patent Document 1, Patent Document 2). A carbodiimide compound is used as the sealant for carboxyl groups.

However, as the carbodiimide compound is a linear compound, foul odors are produced from a volatile isocyanate compound which is formed as a by-product when the carbodiimide compound is used, thereby worsening the work environment.

To cope with this, the applicant found a cyclic carbodiimide compound as a sealant which does not form an isocyanate compound as a by-product even when it reacts with a carboxyl group and filed an international patent application for this (Patent Document 3). However, an industrial process for the production of this useful cyclic carbodiimide compound is not established yet.
(Patent Document 1) JP-A 2004-332166
(Patent Document 2) JP-A 2005-350829
(Patent Document 3) PCT/JP2009/071190

DISCLOSURE OF THE INVENTION

Production Process of Carbodiimide (C)

It is an object of the present invention to establish a technology for obtaining a high-purity carbodiimide from a specific amine through a thiourea efficiently by using an industrially applicable method.

A general method used to obtain a thiourea (B) represented by the following formula (B) which is the precursor of a carbodiimide (C) represented by the following formula (C) is to react an amine (A) represented by the following formula (A) with carbon disulfide so as to remove hydrogen sulfide. However, in general, a reaction between an arylamine and carbon disulfide is very slow and has low yield. Further, since a large amount of a base is required and the reaction takes long, the above method has a problem with productivity. In addition, a large-scale removing apparatus for capturing hydrogen sulfide which is formed as a by-product in a stoichiometric amount is required.

A general method used to obtain the carbodiimide (C) from the thiourea (B) is an oxidative desulfurization reaction from the thiourea (B). Although a simple method is to use mercury oxide or lead oxide, it has a great impact on the environment and cannot be used for industrial-scale production. A method in which sulfonyl chloride such as tosyl chloride or methanesulfonyl chloride is caused to act in a basic solvent such as pyridine is commonly used and applicable. However, pyridine is generally expensive and a recovery cycle is required for industrial-scale production but its recovery is difficult due to its compatibility with water and its azeotropic phenomenon. Sulfonyl chloride is also generally expensive.

To synthesize a carbodiimide from a thiourea, a method in which a hypochlorite is caused to act is desired from an industrial point of view. However, there is no example in which it is applied to the thiourea (B).

The inventors of the present invention conducted intensive studies to solve the above problems and found (a) a method for obtaining a thiourea from an amine, which can be applied industrially advantageously, (2) a method for obtaining a carbodiimide from a thiourea, which can be applied industrially advantageously, and (3) a method for purifying a carbodiimide. They found that a high-purity carbodiimide can be obtained efficiently by a combination of these methods as a method which allows for the industrial-scale production of the carbodiimide.

That is, it is an object of the present invention to provide a process for a production of a carbodiimide, comprising steps of:
(1) reacting an amine represented by the following formula (A) with carbon disulfide in the presence of a catalyst at a reaction temperature of 50 to 150° C. to obtain a thiourea represented by the following formula (B):

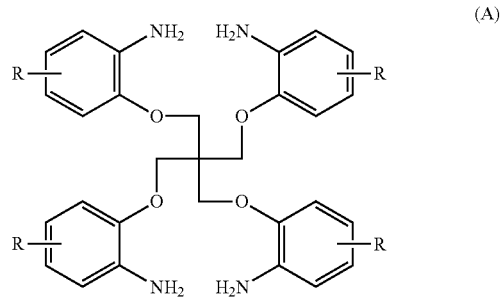

(A)

(In the above formula (A), R is a hydrogen atom or an alkyl group having 1 to 6 carbon atoms.)

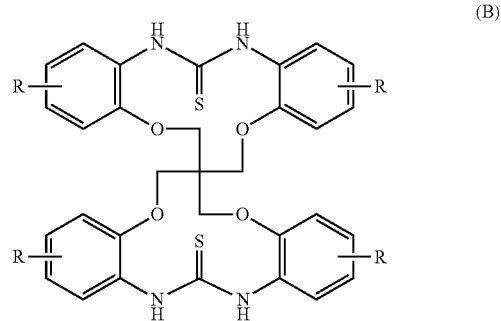

(B)

(In the above formula (B), R is as defined in the above formula (A).);
(2) desulfurizing the obtained thiourea with a hypochlorite in the presence of a basic compound to obtain a carbodiimide represented by the following formula (C):

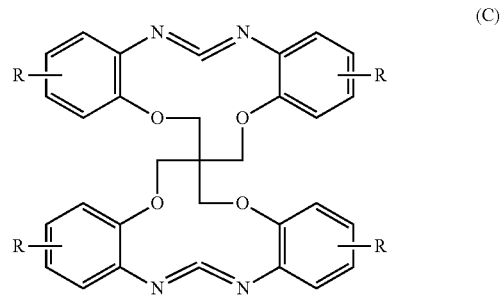

(C)

(In the above formula (C), R is as defined in the above formula (A).); and
(3) purifying the obtained carbodiimide.

The invention of the present application also includes the following inventions.

2. The production process in the above paragraph 1, wherein the step (1) is carried out in the presence of a hydrogen sulfide capture agent.
3. The production process in the above paragraph 1, wherein the step (1) is carried out in a sealed condition.
4. The production process in the above paragraph 1, wherein the catalyst used in the step (1) is a compound having basicity with a pKa of its conjugate acid of 5 or more.
5. The production process in the above paragraph 4, wherein the compound having basicity with a pKa of its conjugate acid of 5 or more is a substituted tertiary amine, a substituted imine, a substituted amide or a substituted heterocyclic ring.
6. The production process in the above paragraph 1, wherein a phase transfer catalyst represented by the following formula (i) is further used in the step (2).

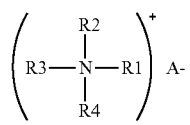
(i)

(In the above formula (i), R1 to R4 are each independently a group selected from an alkyl group having 1 to 20 carbon atoms, an aryl group having 6 to 20 carbon atoms and an aralkyl group having 7 to 20 carbon atoms. A⁻ is a halogen anion.)

7. The production process in the above paragraph 1, wherein the hypochlorite used in the step (2) is sodium hypochlorite.
8. The production process in the above paragraph 1, wherein the basic compound in the step (2) is sodium hydroxide, potassium hydroxide or a mixture thereof.
9. The production process in the above paragraph 1, wherein the purification of the step (3) is recrystallization or extraction.

<Production Process of Amine Represented by Formula (A)>

It is another object of the present invention to provide a process for obtaining an amine, comprising the steps of:

reacting a compound represented by the following formula (a) with a compound represented by the following formula (b) to obtain a nitro represented by the following formula (c); and reducing the nitro.

Especially, when the nitro represented by the formula (c) is synthesized, a method which can be applied industrially advantageously is used to improve the reaction yield.

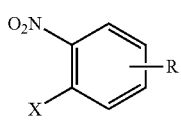
(a)

(In the above formula (a), R is a hydrogen atom or an alkyl group having 1 to 6 carbon atoms. X is a halogen atom or a nitro group.)

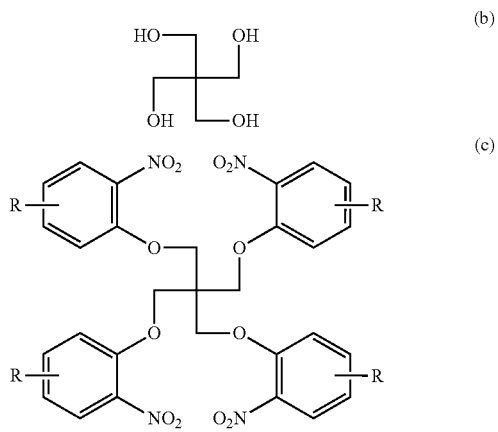

(In the above formula (c), R is as defined in the above formula (a).)

As a general method used to obtain the compound (c), a method in which an elimination group is introduced into the compound (b) to be reacted with substituted-o-nitrophenol or a method in which the compound (b) is reacted with substituted-o-halonitrobenzene can be employed.

Although the latter method is particularly useful, a method in which a solid basic compound is caused to act in an aprotic polar solvent is generally used. The aprotic polar solvent is typified by N,N-dimethylformamide, N-methylpyrrolidone and dimethyl sulfoxide. They are generally expensive and require a recovery cycle for industrial-scale production. However, since they have compatibility with water and high boiling point, it is difficult to recover them and a huge amount of energy is required. The solid basic compound is generally typified by potassium carbonate, sodium hydride, sodium hydroxide and potassium hydroxide, and attention must be paid to its deliquescent property, an explosion hazard caused by the production of hydrogen and the handling of strong alkaline dust in many cases.

The inventors studied the means of improving the reaction yield by employing an industrially advantageous method when the nitro represented by the formula (c) is synthesized by reacting the compound represented by the formula (a) with the compound represented by the formula (b). As a result, they found that a nitro having high purity can be produced at a high yield without using an aprotic polar solvent when a specific catalyst and an aqueous solution of an alkaline metal hydroxide are made existent during a reaction. The present invention was accomplished based on this finding.

That is, before the step (1), the process of the present invention preferably comprises the steps of:

(α) reacting a compound represented by the following formula (a) with a compound represented by the following formula (b) in the presence of a phase transfer catalyst and an aqueous solution of an alkali metal hydroxide to obtain a nitro represented by the following formula (c):

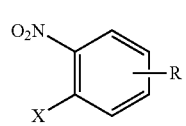
(a)

(In the above formula (a), R is a hydrogen atom or an alkyl group having 1 to 6 carbon atoms. X is a halogen atom or a nitro group.)

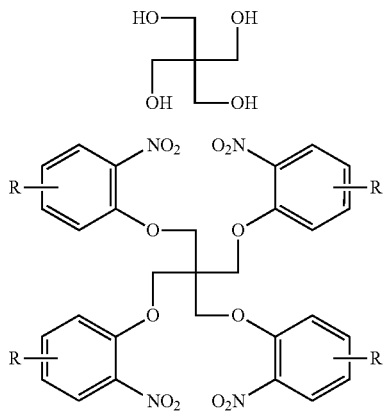

(In the above formula (c), R is as defined in the above formula (a).); and (β) reducing the obtained nitro represented by the formula (c) to obtain an amine represented by the following formula
(A):

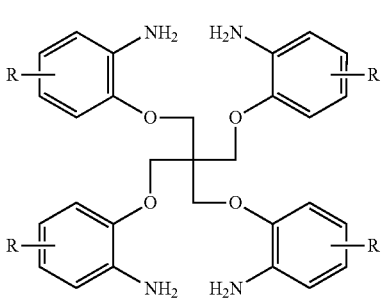

(In the above formula (A), R is as defined in the above formula (a.).

11. The phase transfer catalyst is preferably a compound represented by the following formula (i).

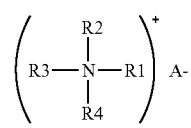

(In the above formula (i), R1 to R4 are each independently a group selected from an alkyl group having 1 to 20 carbon atoms, an aryl group having 6 to 20 carbon atoms and an aralkyl group having 7 to 20 carbon atoms. A⁻ is a halogen anion.)

12. The phase transfer catalyst is at least one compound selected from the group consisting of tetraethylammonium salts, tetrabutylammonium salts, trioctylmethylammonium salts, benzyldimethyloctadecylammonium salts, benzyltriethylammonium salts, benzyltrimethylammonium salts and benzyltributylammonium salts.

13. The aqueous solution of an alkaline metal hydroxide is preferably a sodium hydroxide aqueous solution or a potassium hydroxide aqueous solution.

BEST MODE FOR CARRYING OUT THE INVENTION

<Production Process of Carbodiimide>

The production process of the carbodiimide of the present invention comprises the steps (1), (2) and (3).

[Step (1)]

The step (1) is to react an amine represented by the following formula (A) with carbon disulfide at a reaction temperature of 50 to 150° C. in the presence of a catalyst to obtain a thiourea represented by the following formula (B).

The amine is represented by the following formula (A).

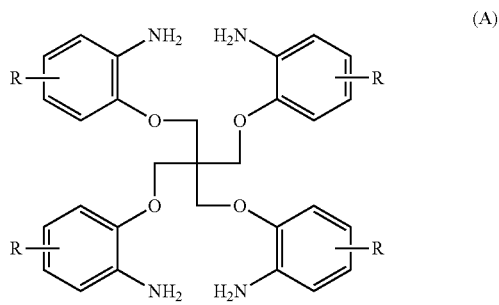

In the above formula (A), R is a hydrogen atom or an alkyl group having 1 to 6 carbon atoms. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

The catalyst is preferably a compound having basicity with a pKa of its conjugate acid of 5 or more. The compound is selected from a substituted tertiary amine, a substituted alkanolamine, a substituted imine, a substituted amide and a substituted heterocyclic ring. Specific examples thereof include triethylamine, N-methylpyrrolidone, N-methylmorpholine, tetramethylethylenediamine, dimethylethanolamine, diethylethanolamine, ethyldiethanolamine, butyldiethanolamine, triethanolamine, imidazole, N-methyl-2-mercaptoimidazole, pyridine, 4-dimethylaminopyridine, tetramethylguanidine, 1,8-diazabicyclo[5.4.0]undec-7-ene and 1,4-diazabicyclo[2.2.2]octane.

The amount of the catalyst is preferably 0.1 to 5 moles, more preferably 0.3 to 3 moles based on 1 mole of the amine. The amount of carbon disulfide is preferably 2 to 8 moles, more preferably 3 to 6 moles based on 1 mole of the amine.

The reaction is preferably carried out under a sealed condition. The reaction temperature is 50 to 150° C., preferably 80 to 130° C. By carrying out the reaction under a sealed condition, the reaction system can be heated without being affected by low-boiling point carbon disulfide and the reaction can be promoted quickly. The reaction time is 3 to 20 hours preferably 5 to 15 hours.

The reaction is preferably carried out in the presence of a hydrogen sulfide capture agent. The hydrogen sulfide capture agent means a compound which can react with hydrogen sulfide, as exemplified by alkyl halides, acid anhydrides and multiply-bonded compounds. Multiply-bonded compounds are preferred when the odors of by-product acid and mercaptan and reactivity with a raw material amine are taken into consideration. Nitrile compounds may be preferably used, out of which acetonitrile and benzonitrile are used and may also be used as a solvent.

After the end of the reaction, excessive carbon disulfide is contained. Although it may not be removed, its concentration and removal are preferred before filtration from the viewpoint of safety. A solvent may be added thereafter. The recovered carbon disulfide can be recycled to the production system.

In the step (1), the amount of the basic compound may be the amount of a catalyst, a thiourea of interest can be obtained in a short time, and most of the desorbed hydrogen sulfide is captured by a capture agent and not discharged to the outside of the system, whereby a large-scale apparatus for removing hydrogen sulfide is not necessary.

When a preferably used nitrile is used as the capture agent, after its reaction with hydrogen sulfide, it becomes a thioamide which is chemically neutral and stable, thereby making a treatment after that simple.

The thiourea obtained in the step (1) is represented by the following formula (B).

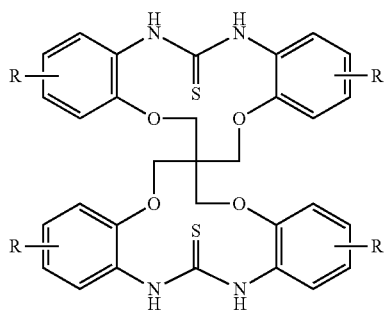

(B)

In the formula (B), R is as defined in the above formula (A).

[Step (2)]

The step (2) is to desulfurize the obtained thiourea with a hypochlorite in the presence of a basic compound to obtain a carbodiimide represented by the following formula (C).

As the basic compound is used sodium hydroxide, potassium hydroxide or a mixture thereof. It may be added continuously or in fractional amounts. The amount of the basic compound is preferably 0.3 to 6 equivalents, more preferably 0.5 to 4 equivalents based on the thiourea. The basic compound is preferably in the form of an aqueous solution. The concentration of the aqueous solution is preferably 60 to 10 wt %, more preferably 50 to 20 wt % which is easily industrially acquired.

An example of the hypochlorite is sodium hydrochlorite. The amount of the hypochlorite is preferably 2 to 10 equivalents, more preferably 3 to 5 equivalents based on the thiourea. The hypochlorite is preferably in the form of an aqueous solution. The concentration of the aqueous solution is preferably 15 to 10 wt % which is easily industrially acquired.

The reaction is preferably carried out in an organic solvent. An organic solvent which is separated from water is preferably used, as exemplified by chloroform, toluene, chlorobenzene and xylene. The amount of the organic solvent is preferably 2 to 15 times, more preferably 3 to 8 times the weight of the thiourea. These solvents may be used alone but a polar solvent such as methanol, ethanol, isopropanol or propanol may be added to promote the reaction smoothly.

In the step (2), a phase transfer catalyst is preferably used to promote the reaction smoothly. As the phase transfer catalyst may be used an ordinary quaternary ammonium salt. A compound represented by the following formula (i) is preferably used as the phase transfer catalyst.

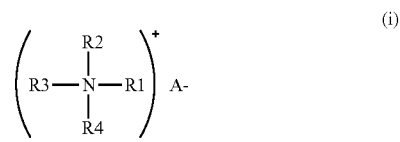

(i)

In the formula (i), R1 to R4 are each independently a group selected from an alkyl group having 1 to 20 carbon atoms, an aryl group having 6 to 20 carbon atoms and an aralkyl group having 7 to 20 carbon atoms. A⁻ is a halogen anion.

Examples of the alkyl group having 1 to 20 carbon atoms include methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, octadecyl group and nonadecyl group. Examples of the aryl group having 6 to 20 carbon atoms include phenyl group and naphthyl group. They may be substituted by an alkyl group having 1 to 10 carbon atoms. Examples of the alkyl group having 1 to 10 carbon atoms as a substituent include methyl group, ethyl group, propyl group, butyl group, pentyl group, hexyl group, heptyl group, octyl group, nonyl group and decyl group. Examples of the aralkyl group having 7 to 20 carbon atoms include benzyl group, phenethyl group, methylbenzyl group and diphenylmethyl group. Examples of the halogen anion A⁻ include fluorine ion, chlorine ion and bromine ion.

Examples of the phase transfer catalyst include tetraethylammonium salts, tetrabutylammonium salts, trioctylmethylammonium salts, benzyldimethyloctadecylammonium salts, benzyltriethylammonium salts, benzyltrimethylammonium salts and benzyltributylammonium salts. They may be used alone or in combination of two or more. A quaternary ammonium salt may be used as the phase transfer catalyst. The amount of the phase transfer catalyst is 0.01 to 0.2 times, more preferably 0.03 to 0.1 time the weight of the thiourea.

The carbodiimide obtained in the step (2) is represented by the following formula (C).

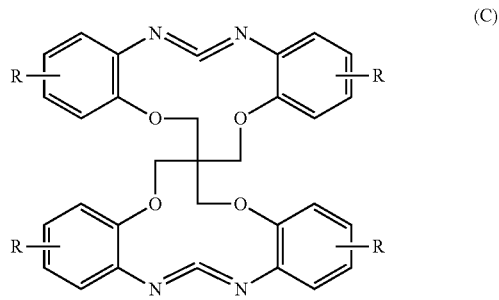

(C)

In the formula (C), R is as defined in the above formula (A).

After the end of the reaction, the organic solvent may be concentrated and replaced by a new organic solvent so as to improve the yield and quality of the compound C. That is, this step may include the subsequent step (3). As a matter of course, the method of synthesizing this carbodiimide, that is, the step (2) can be applied to the thiourea synthesized without the step (1).

[Step (3)]

The step (3) is to purify the obtained carbodiimide. Sulfur is contained in the carbodiimide obtained from the thiourea in many cases. The color tone and purity of the carbodiimide are improved by purification.

Purification is preferably recrystallization or extraction. Purification is carried out by heating the carbodiimide in an organic solvent to extract unwanted substances including a coloring component, cooling, filtering and washing it.

Any organic solvent may be acceptable if it has solubility for sulfur in a minute amount and is selected from aromatic hydrocarbons, hydrogen carbide, ethers, ketones, esters, alcohols and halogen-containing solvents. Specific examples of the organic solvent include toluene, xylene, chlorobenzene, dichlorobenzene, chlorotoluene, hexane, heptane, cyclohexane, tetrahydrofuran, acetone, methyl ethyl ketone, ethyl acetate, methanol, ethanol, dichloromethane and chloroform. Toluene, xylene, chlorobenzene, tetrahydrofuran and chloroform are preferably used from the viewpoints of the amount of the solvent, a depigmentation effect, the removal rate of sulfur and the recovery rate of the carbodiimide.

The amount of the organic solvent is preferably 2 to 50 times, more preferably 3 to 15 times the weight of the carbodiimide. After heating, the organic solvent used to increase the recovery rate of the carbodiimide may be concentrated and recovered.

As a matter of course, the purity and color of even a carbodiimide synthesized without the steps (2) and (3) are improved by the process of the present invention. The process of the present invention is particularly effective for the purification of a carbodiimide synthesized through a thiourea.

<Production of Amine Represented by Formula (A)>

The amine represented by the formula (A) can be produced by the following steps:

(α) reacting a compound represented by the following formula (a) with a compound represented by the following formula (b) in the presence of a phase transfer catalyst and an aqueous solution of an alkali metal hydroxide to obtain a nitro represented by the following formula (c); and (β) reducing the obtained nitro represented by the formula (c) to obtain an amine represented by the formula (A).

[Step (α)]

The compound (a) is represented by the following formula.

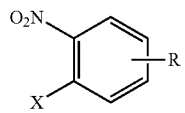

In the formula (a), R is a hydrogen atom or an alkyl group having 1 to 6 carbon atoms. X is a halogen atom or a nitro group. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group. Examples of the halogen atom include chlorine atom, bromine atom and iodine atom.

As the compound (a) is preferably used o-chloronitrobenzene, o-fluoronitrobenzene or o-dinitrobenzene. They may be substituted. The amount of the compound (a) is preferably 4 to 8 equivalents, more preferably 4 to 6 equivalents based on the compound (b).

The compound (b) is pentaerythritol represented by the following formula.

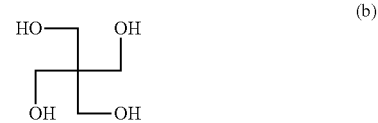

The nitro is represented by the following formula (c).

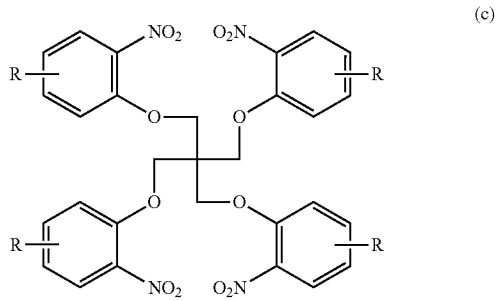

In the formula (c), R is as defined in the formula (a), that is, a hydrogen atom or an alkyl group having 1 to 6 carbon atoms. Examples of the alkyl group having 1 to 6 carbon atoms include methyl group, ethyl group, n-propyl group, sec-propyl group, iso-propyl group, n-butyl group, tert-butyl group, sec-butyl group, iso-butyl group, n-pentyl group, sec-pentyl group, iso-pentyl group, n-hexyl group, sec-hexyl group and iso-hexyl group.

The characteristic feature of the step (α) is that the above compound (a) is reacted with the compound (b) in the presence of a phase transfer catalyst and an aqueous solution of an alkali metal hydroxide. The phase transfer catalyst in the step (α) is preferably a compound represented by the following formula (i).

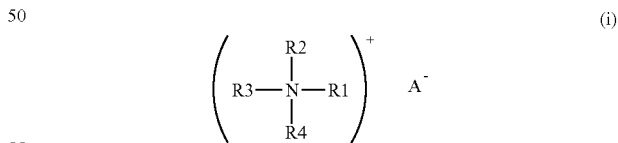

In the formula (i), R1 to R4 are each independently a group selected from an alkyl group having 1 to 20 carbon atoms, an aryl group having 6 to 20 carbon atoms and an aralkyl group having 7 to 20 carbon atoms. A⁻ is a halogen anion.

Examples of the alkyl group having 1 to 20 carbon atoms include methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, octadecyl group and nonadecyl group. Examples of the aryl group having 6 to 20 carbon atoms include phenyl group and naphthyl group. They may be substituted by an alkyl group having 1 to 10 carbon atoms. Examples of the alkyl group having 1 to 10 carbon atoms as a substituent include methyl group, ethyl group, propyl group, butyl group, pentyl group, hexyl group, heptyl group, octyl group, nonyl group and decyl group. Examples of the aralkyl group having 7 to 20 carbon atoms include benzyl group, phenethyl group, methylbenzyl group and diphenylmethyl group. Examples of the halogen anion $A^-$ include fluorine ion, chlorine ion and bromine ion.

Examples of the phase transfer catalyst include tetraethylammonium salts, tetrabutylammonium salts, trioctylmethylammonium salts, benzyldimethyloctadecylammonium salts, benzyltriethylammonium salts, benzyltrimethylammonium salts and benzyltributylammonium salts. They may be used alone or in combination of two or more. A quaternary ammonium salt may be used as the phase transfer catalyst. The amount of the phase transfer catalyst may be 0.1 to 5 equivalents based on the compound (b).

Examples of the alkali metal include sodium and potassium. As the aqueous solution of an alkali metal hydroxide may be preferably used a sodium hydroxide aqueous solution and a potassium hydroxide aqueous solution. The concentration of the aqueous solution is preferably 60 to 20 wt %, more preferably 48 to 30 wt % which can be industrially acquired.

The aqueous solution of an alkali metal hydroxide is preferably a sodium hydroxide aqueous solution or a potassium hydroxide aqueous solution. The aqueous solution of the alkali metal hydroxide may be added continuously or in fractional amounts. The amount of the aqueous solution of the alkali metal hydroxide is preferably 4 to 15 equivalents, preferably 4.5 to 10 equivalents based on the compound (b) as an alkali metal hydroxide when the proceeding and economic efficiency of the reaction are taken into consideration.

The aqueous solution of the alkali metal hydroxide is easy to handle and inexpensive as compared with a solid basic compound such as potassium carbonate, sodium hydride, sodium hydroxide or potassium hydroxide.

Although a small amount of the organic solvent may be added to the reaction system from the viewpoints of the sublimation and melting point of the compound (a), as a matter of course, the reaction can be carried out without a solvent. After the end of the reaction, the reaction solution has strong alkalinity and may or may not be neutralized with an acid. Washing after filtration is preferably carried out with water so as to wash away water-soluble impurities. Thereafter, an organic solvent, especially toluene or methanol which is often used in the industrial field can be used to wash away impurities such as raw materials. These organic solvents can be recycled to the production system. Since an expensive aprotic polar solvent is not used in this reaction system, the recovery of the solvent is naturally unnecessary, and the amine can be produced industrially advantageously.

[step (β)]

The step (β) is to reduce the obtained nitro represented by the formula (c) so as to obtain an amine represented by the formula (A).

The reaction can be carried out by using a conventionally known method. For example, the nitro (c) is contact reduced in a solvent in the presence of hydrogen and a catalyst.

Examples of the catalyst include palladium carbon, palladium carbon-ethylenediamine complex, palladium-fibroin, palladium-polyethyleneimine, nickel and copper. Examples of the solvent include methanol, ethanol, isopropyl alcohol, dioxane, tetrahydrofuran, ethyl acetate, dichloromethane, chloroform and N,N-dimethylformamide. The reaction temperature is preferably 25 to 100° C. Although the reaction proceeds at normal pressure, pressure is preferably applied to promote the reaction.

Alternatively, a method in which the nitro (c) is reacted with an acid and a metal or a method in which the nitro (c) is reacted with hydrazine and a catalyst may be employed to obtain the amine (A).

EXAMPLES

<Production Process of Carbodiimide>

The production process of the carbodiimide (C) will be described in detail hereinunder. Values were obtained by the following methods.

(1) Identification of compound:

The identification of each compound was carried out by means of the GCMS-QP5000 mass analyzer of Shimadzu Corporation.

(2) Yield, yield rate:

The yields and yield rates of the synthesized intermediate and the final product were calculated based on the raw material amine in the case of a thiourea, based on the raw material thiourea in the case of a carbodiimide and based on a carbodiimide before purification in the case of a purified carbodiimide.

(3) LC purity:

LC purity indicates the area percent of each compound based on 100% of the total area value of peaks excluding the solvent by confirming with analysis using high-speed liquid chromatography.

(4) Sulfur content:

This was measured by using high-speed liquid chromatography.

(5) Color tone:

The color tone was measured with a color difference meter by grinding a specimen.

Color difference meter: Spectro Color Meter SE2000 of Nippon Denshoku Industries Co., Ltd.

Example 1

[Step (1)]

100.0 g (0.2 mole) of an amine (A1) of the formula (A) in which R is a hydrogen atom (manufactured by Kawaguchi Chemical Industry Co., Ltd.: LC purity of 96%), 91.2 g (1.2 moles) of carbon disulfide, 8.96 g (0.1 mole) of dimethylethanolamine and 450 ml of acetonitrile were added to an SUS autoclave which was then sealed up. Thereafter, a reaction was carried out at 100° C. for 15 hours under agitation. After cooling, the pressure was relieved, and excessive carbon disulfide was collected. Thereafter, 100 ml of acetonitrile was added, the resulting mixture was filtered, and the filtrate was washed with 500 ml of acetonitrile. After drying, a thiourea (B1) of the formula (B) in which R is a hydrogen atom was obtained. (yield: 107.6 g/yield rate: 92.0%/LC purity: 97.8%)

[Step (2)]

50.0 g (0.086 mole) of the obtained thiourea (B1), 1,200 g of chloroform, 40 g of methanol, 13.2 g (0.1 mole) of a 30% sodium hydroxide aqueous solution and 3.0 g of benzyltriethylammonium chloride were fed. 165.6 g (0.31 mole) of a 13.9% sodium hypochlorite aqueous solution was added dropwise to the obtained product over 50 minutes to ensure that the inside temperature of the reactor did not exceed 40° C. After 1 hour of agitation, 50.0 g of the thiourea (B1) and 13.2 g of a 30% sodium hydroxide aqueous solution were injected again. 165.6 g of a 13.9% sodium hypochlorite aqueous solution was added dropwise at a reactor inside temperature of 25 to 40° C. over 50 minutes. After 3.5 hours of agitation at 30 to 40° C., chloroform was distilled off under reduced pressure, and 300 g of toluene was added. The content was filtered, and the filtrate was washed with 200 g of water, 100 g of toluene and 160 g of acetone sequentially. After drying, a carbodiimide (C1) of the formula (C) in which R is a hydrogen atom was obtained. (yield: 73.3 g/yield rate: 82.9%/LC purity: 99.0%/sulfur content: 394 ppm) (color tone: Lab/YI: 86.65, 2.00, 10.38/23.31)

[Step (3)]

5.00 g of the obtained carbodiimide (C1) and 15 ml of toluene were fed and refluxed for 3 hours. After cooling, the obtained product was filtered, and the filtrate was washed with 10 ml of acetone. After drying, a purified carbodiimide (C1) of the formula (C) in which R is a hydrogen atom was obtained. (yield: 4.75 g/yield rate: 95.0%). At this point, the sulfur content was reduced to 123 ppm, and the LC purity was 99.3%. (color tone: Lab/YI: 90.50, −0.19, 6.96/13.83)

Example 2

A purified carbodiimide (C1) was obtained in the same manner as in Example 1 except that the carbodiimide (C1) of the formula (C) in which R is a hydrogen atom, obtained from the steps (1) and (2), was used and toluene in the step (3) was changed to tetrahydrofuran. (yield: 4.50 g/yield rate: 90.0%). At this point, the sulfur content was reduced to 73 ppm and the LC purity was 99.9%. (color tone: Lab/YI: 91.83, 0.09, 7.30/14.51)

Example 3

A purified carbodiimide (C1) was obtained in the same manner as in Example 1 except that the carbodiimide (C1) of the formula (C) in which R is a hydrogen atom, obtained from the steps (1) and (2), was used and toluene in the step (3) was changed to chloroform. (yield: 4.66 g/yield rate: 93.2%). At this point, the sulfur content was reduced to 216 ppm and the LC purity was 99.3%. (color tone: Lab/YI: 91.45, 0.15, 8.20/16.38)

Example 4

A purified carbodiimide (C1) was obtained in the same manner as in Example 1 except that the carbodiimide (C1) of the formula (C) in which R is a hydrogen atom, obtained from the steps (1) and (2), was used and toluene in the step (3) was changed to 20 ml of methyl ethyl ketone. (yield: 4.71 g/yield rate: 94.2%). At this point, the sulfur content was reduced to 223 ppm and the LC purity was 99.3%. (color tone: Lab/YI: 91.47, 0.42, 8.42/17.03)

Example 5

5.00 g of the carbodiimide (C1) of the formula (C) in which R is a hydrogen atom, obtained from the steps (1) and (2) in Example 1, and 75 ml of toluene were fed and refluxed for 1 hour. Thereafter, 40 ml of toluene was concentrated. After cooling, the obtained product was filtered and the filtrate was washed with 10 ml of acetone. After drying, a purified carbodiimide (C1) of the formula (C) in which R is a hydrogen atom was obtained. (yield: 4.70 g/yield rate: 94.0%). At this point, the sulfur content was reduced to 9 ppm and the LC purity was 99.5%.

Example 6

[Step (1)]

40.0 g (0.08 mole) of an amine (A1) of the formula (A) in which R is a hydrogen atom (manufactured by Kawaguchi Chemical Industry Co., Ltd.: LC purity of 96%), 36.6 g (0.48 mole) of carbon disulfide, 10.9 g (0.16 mole) of imidazole and 120 ml of acetonitrile were added to an SUS autoclave which was then sealed up. Thereafter, a reaction was carried out at 100° C. for 15 hours under agitation. After cooling, the pressure was relieved, and excessive carbon disulfide was collected by distillation. Thereafter, 50 ml of acetonitrile was added, the resulting mixture was filtered, and the filtrate was washed with 200 ml of acetonitrile. A thiourea (B1) of the formula (B) in which R is a hydrogen atom was obtained. (yield before drying: 47.6 g/yield rate: 101.8%/LC purity: 97.6%)

[Step (2)]

9.0 g (pure content of 0.013 mole) of the obtained undried thiourea (B1), 90 g of chloroform, 3 g of methanol, 2.0 g (0.015 mole) of a 30% sodium hydroxide aqueous solution and 0.45 g of benzyltriethylammonium chloride were fed. 25.1 g (0.047 mole) of a 13.9% sodium hypochlorite aqueous solution was added dropwise to the obtained product over 25 minutes to ensure that the inside temperature of the reactor did not exceed 40° C. After 1 hour of agitation, 9.0 g of the obtained thiourea (B1) before drying and 2.0 g of a 30% sodium hydroxide aqueous solution were injected again. 25.1 g of a 13.9% sodium hypochlorite aqueous solution was added dropwise at a reactor inside temperature of 25 to 40° C. over 15 minutes. After 4 hours of agitation at 30 to 40° C., chloroform was distilled off under reduced pressure and 45 g of toluene was added. The content was filtered and the filtrate was washed with 30 g of water, 15 g of toluene and 25 g of acetone sequentially. After drying, a carbodiimide (C1) of the formula (C) in which R is a hydrogen atom was obtained. (yield: 11.8 g/yield rate: 88.7%/LC purity: 98.8%/sulfur content: 1018 ppm)

[Step (3)]

5.00 g of the obtained carbodiimide (C1) and 50 ml of toluene were fed and refluxed for 3 hours. After cooling, the obtained product was filtered and the filtrate was washed with 10 ml of acetone. After drying, a purified carbodiimide (C1) of the formula (C) in which R is a hydrogen atom was obtained. (yield: 4.53 g/yield rate: 90.6%). At this point, the sulfur content was reduced to 47 ppm and the LC purity was 99.4%.

<Production of Amine Represented by Formula (A)>

The production process of the amine represented by the formula (A) will be described hereinunder. Values were obtained by the following methods.

(1) Identification of compound:

The identification of each compound was carried out by means of the JNR-EX270 NMR of JEOL Ltd. and the GCMS-QP5000 mass analyzer of Shimadzu Corporation.

(2) Yield, yield rate:

The yield and yield rate of the synthesized nitro were calculated based on the compound (b).

(3) LC purity:

The LC purity indicates the area percent of the compound (c) based on 100% of the total area value of peaks excluding the solvent and the raw material compound (a) by confirming with analysis using high-speed liquid chromatography.

(4) Selectivity:

The selectivity is represented by area value of tetranitro/(area value of tetranitro+area value of trinitromonohalogen)×100

The area values of the tetranitro and the trinitromonohalogen were obtained by analysis using high-speed liquid chromatography.

Synthesis Example 1

[Step (α)]

4.08 g of pentaerythritol, 23.63 g of o-chloronitrobenzene, 4 ml of toluene and 6.83 g of benzyltriethylammonium chloride were fed to a glass reactor, and 31.56 g of a 48% potassium hydroxide aqueous solution was added to the reactor at 70 to 85° C. over 5 hours. Thereafter, a reaction was carried out at the same temperature for 20 hours. After cooling, 50 g of water was added to the reaction product, and the resulting product was neutralized with hydrochloric acid. Thereafter, the obtained product was filtered, and the filtrate was washed with 60 g of water and 90 ml of methanol sequentially and dried to obtain a nitro (c). (yield: 17.90 g/yield rate: 96.2%/LC purity: 96.7%/selectivity: 97.7%). The obtained nitro (c) had a high yield rate and high purity.

[Step (β)]

Then, the nitro (c) (0.1 mole), 5% palladium carbon (Pd/C) (2 g) and 400 ml of ethanol/dichloromethane (70/30) were fed to a reactor equipped with a stirrer, the inside of the reactor was substituted by hydrogen 5 times, and a reaction was carried out while hydrogen was always supplied at 25° C. and terminated when the amount of hydrogen did not decrease any more. When Pd/C was collected and the mixed solvent was removed, an amine (A) was obtained.

Synthesis Example 2

[Step (α)]

4.08 g of pentaerythritol, 23.63 g of o-chloronitrobenzene, 4 ml of toluene, 4.5 g of water and 6.96 g of tetrabutylammonium bromide were fed to a glass reactor, and 22.5 g of a 48% sodium hydroxide aqueous solution was added to the reactor at 80 to 84° C. over 4 hours and 40 minutes. Thereafter, a reaction was carried out at the same temperature for 22 hours. After cooling, 40 g of water and 4 ml of toluene were added to the reaction product, and the resulting product was neutralized with hydrochloric acid. Thereafter, the obtained product was filtered, and the filtrate was washed with 40 g of water and 60 ml of methanol sequentially and dried to obtain a nitro (c). (yield: 17.89 g/yield rate: 96.1%/LC purity: 95.9%/selectivity: 96.4%). The obtained nitro (c) had a high yield rate and high purity.

[Step (β)]

Then, the nitro (c) (0.1 mole), 5% palladium carbon (Pd/C) (2 g) and 400 ml of ethanol/dichloromethane (70/30) were fed to a reactor equipped with a stirrer, the inside of the reactor was substituted by hydrogen 5 times, and a reaction was carried out while hydrogen was always supplied at 25° C. and terminated when the amount of hydrogen did not decrease any more. When Pd/C was collected and the mixed solvent was removed, an amine (A) was obtained.

Synthesis Example 3

[step (α)]

1.36 g of pentaerythritol, 6.77 g of o-fluoronitrobenzene, 2.5 ml of toluene, 0.77 g of tetrabutylammonium bromide and 9.35 g of 48% potassium hydroxide were fed to a glass reactor to carry out a reaction at 70° C. for 18 hours. After cooling, the reaction product was neutralized with concentrated hydrochloric acid and then 7.5 ml of toluene was added. Thereafter, the obtained product was filtered, and the filtrate was washed with 20 ml of water and 60 ml of methanol and dried to obtain a nitro (c). (yield: 6.18 g/yield rate: 99.6%/LC purity: 99.9%/selectivity: 100%). The obtained nitro (c) had a high yield rate and high purity.

[Step (β)]

Then, the nitro (c) (0.1 mole), 5% palladium carbon (Pd/C) (2 g) and 400 ml of ethanol/dichloromethane (70/30) were fed to a reactor equipped with a stirrer, the inside of the reactor was substituted by hydrogen 5 times, and a reaction was carried out while hydrogen was always supplied at 25° C. and terminated when the amount of hydrogen did not decrease any more. When Pd/C was collected and the mixed solvent was removed, an amine (A) was obtained.

Synthesis Example 4

[Step (α)]

0.68 g of pentaerythritol, 4.20 g of o-dinitrobenzene, 3 ml of toluene, 0.38 g of tetrabutylammonium bromide and 3.33 g of sodium hydroxide were fed to a glass reactor to carry out a reaction at 55° C. for 20 hours. After cooling, 10 g of water was added to the reaction product, and the resulting product was neutralized with concentrated hydrochloric acid. Thereafter, the obtained product was filtered, and the filtrate was washed with 20 ml g of water and 30 ml of methanol and dried to obtain a nitro (c). (yield: 2.80 g/yield rate: 90.2%/LC purity: 99.8%). The obtained nitro (c) had a high yield rate and high purity.

[Step (β)]

Then, the nitro (c) (0.1 mole), 5% palladium carbon (Pd/C) (2 g) and 400 ml of ethanol/dichloromethane (70/30) were fed to a reactor equipped with a stirrer, the inside of the reactor was substituted by hydrogen 5 times, and a reaction was carried out while hydrogen was always supplied at 25° C. and terminated when the amount of hydrogen did not decrease any more. When Pd/C was collected and the mixed solvent was removed, an amine (A) was obtained.

Reference Example

No Addition of Phase Transfer Catalyst 0.68 g of pentaerythritol, 3.94 g of o-chloronitrobenzene, 5 ml of toluene and 4.0 g of 30% sodium hydroxide were fed to a glass reactor and reacted under reflux for 24 hours. The compound (c) of interest was not obtained at all.

Comparative Synthesis Example 1.36 g of pentaerythritol, 6.61 g of o-chloronitrobenzene, 13 g of N,N-dimethylacetamide and 2.0 g of solid sodium hydroxide were fed to a glass reactor to carry out a reaction at 60° C. for 23 hours. After cooling, 20 g of water was added to the reaction product, the supernatant solution was discarded, and 30 ml of methanol was added to disperse crystals. After filtration, the filtrate was washed with 30 ml of water and 30 ml of methanol and dried to obtain a nitro (c). (yield: 4.51 g/yield rate: 72.7%/LC purity: 77.4%/selectivity: 95.2%). The obtained nitro (c) had a low yield rate and low purity.

Effect of the Invention

According to the production process of the present invention, a high-purity carbodiimide which is useful as an end-sealing agent for polyesters can be produced efficiently. According to the production process of the present invention, a specific nitro which is useful as an intermediate for a cyclic carbodiimide compound can be produced at a high yield.

The invention claimed is:

1. A process for a production of a carbodiimide, comprising steps of:
(1) reacting an amine represented by the following formula (A) with carbon disulfide in the presence of a catalyst at a reaction temperature of 50 to 150° C. to obtain a thiourea represented by the following formula (B):

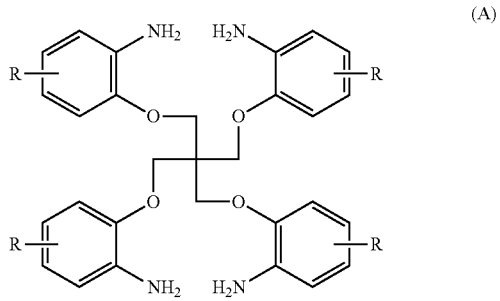

(A)

wherein in the above formula (A), R is a hydrogen atom or an alkyl group having 1 to 6 carbon atoms;

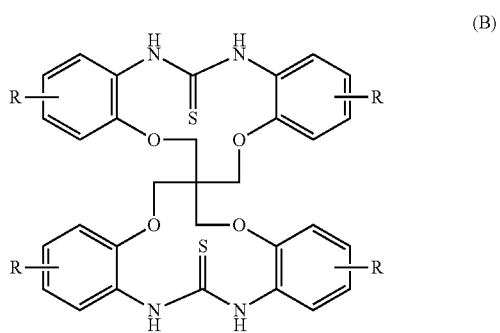

(B)

wherein in the above formula (B), R is as defined in the above formula (A);
(2) desulfurizing the obtained thiourea with a hypochlorite in the presence of a basic compound to obtain a carbodiimide represented by the following formula (C):

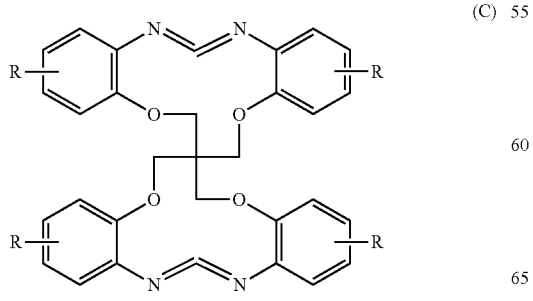

(C)

wherein in the above formula (C), R is as defined in the above formula (A); and
(3) purifying the obtained carbodiimide;
wherein the step (1) is carried out in a sealed condition.

2. The production process according to claim 1, wherein the step (1) is carried out in the presence of a hydrogen sulfide capture agent.

3. The production process according to claim 1, wherein the catalyst used in the step (1) is a compound having basicity with a pKa of its conjugate acid of 5 or more.

4. The production process according to claim 3, wherein the compound having basicity with a pKa of its conjugate acid of 5 or more is a substituted tertiary amine, a substituted imine, a substituted amide or a substituted heterocyclic ring.

5. The production process according to claim 1, wherein a phase transfer catalyst represented by the following formula (i) is further used in the step (2):

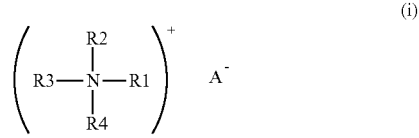

(i)

wherein in the above formula (i), R1 to R4 are each independently a group selected from an alkyl group having 1 to 20 carbon atoms, an aryl group having 6 to 20 carbon atoms and an aralkyl group having 7 to 20 carbon atoms, and A$^-$ is a halogen anion.

6. The production process according to claim 1, wherein the hypochlorite used in the step (2) is sodium hypochlorite.

7. The production process according to claim 1, wherein the basic compound in the step (2) is sodium hydroxide, potassium hydroxide or a mixture thereof.

8. The production process according to claim 1, wherein the purification of the step (3) is recrystallization or extraction.

9. The production process according to claim 1 comprising the following steps before the step (1):
(α) reacting a compound represented by the following formula (a) with a compound represented by the following formula (b) in the presence of a phase transfer catalyst and an aqueous solution of an alkali metal hydroxide to obtain a nitro represented by the following formula (c):

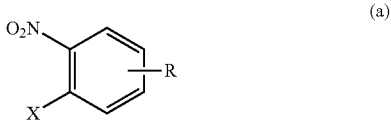

(a)

wherein in the above formula (a), R is a hydrogen atom or an alkyl group having 1 to 6 carbon atoms, and X is a halogen atom or a nitro group;

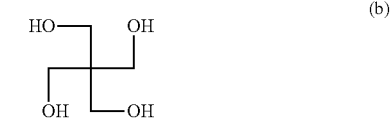

(b)

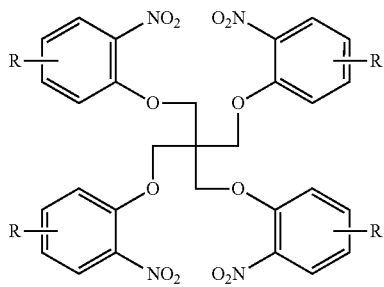
(c)

wherein in the above formula (c), R is as defined in the above formula (a); and (β) reducing the obtained nitro represented by the formula (c) to obtain an amine represented by the following formula (A):

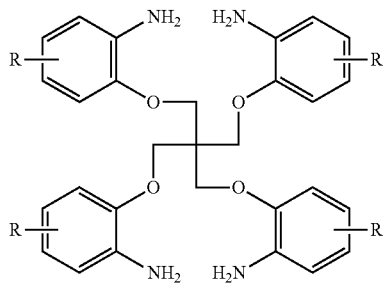
(A)

wherein in the above formula (A), R is as defined in the above formula (a).

10. The production process according to claim 9, where the phase transfer catalyst is a compound represented by the following formula (i):

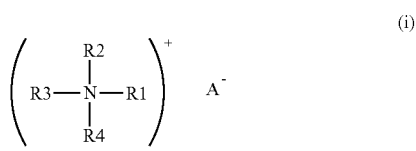
(i)

wherein in the above formula (i), R1 to R4 are each independently a group selected from an alkyl group having 1 to 20 carbon atoms, an aryl group having 6 to 20 carbon atoms and an aralkyl group having 7 to 20 carbon atoms, and $A^-$ is a halogen anion.

11. The production process according to claim 9, wherein the phase transfer catalyst is at least one compound selected from the group consisting of tetraethylammonium salts, tetrabutylammonium salts, trioctylmethylammonium salts, benzyldimethyloctadecylammonium salts, benzyltriethylammonium salts, benzyltrimethylammonium salts and benzyltributylammonium salts.

12. The production process according to claim 9, wherein the aqueous solution of an alkali metal hydroxide is a sodium hydroxide aqueous solution or a potassium hydroxide aqueous solution.

* * * * *